US006211220B1

(12) United States Patent
Pamukcu et al.

(10) Patent No.: US 6,211,220 B1
(45) Date of Patent: Apr. 3, 2001

(54) METHOD FOR TREATING NEOPLASIA WITH AMINO OR PYRIDYLAMINO CYCLOBUTENE DERIVATIVES

(75) Inventors: Rifat Pamukcu, Spring House; Gary A. Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/199,082

(22) Filed: Nov. 23, 1998

(51) Int. Cl.$^7$ .................. A61K 31/415; A61K 31/50; A61K 31/495; A61K 31/505; A61K 31/44; A61K 31/42; A61K 31/405; A61K 31/38

(52) U.S. Cl. .................. 514/399; 514/247; 514/249; 514/256; 514/357; 514/374; 514/375; 514/400; 514/415; 514/438

(58) Field of Search .................. 514/399, 247, 514/249, 256, 357, 374, 394, 375, 400, 415, 438

(56) References Cited

U.S. PATENT DOCUMENTS

| 4,950,680 | 8/1990 | Taylor et al. . |
| 5,696,159 | 12/1997 | Gross et al. . |

FOREIGN PATENT DOCUMENTS

| WO 94/29277 | * 12/1994 | (WO) | .................. 514/399 |
| WO 95/19978 | 7/1995 | (WO) . | |
| WO 00/15222 | 3/2000 | (WO) . | |

OTHER PUBLICATIONS

Blaya, C. et al., Effect of the protein kinase inhibitors, 1-(5-isoquinolinylsulfonyl)-2-methylpiperazine H-7 and N-(2-[methylamino]ethyl)-5-isoquinoline-sulfonamide H-8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC $^{-/-}$ Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

\* cited by examiner

*Primary Examiner*—Jerome D. Goldberg
(74) *Attorney, Agent, or Firm*—Robert W. Stevenson

(57) ABSTRACT

A method for inhibiting neoplasia, particularly cancerous and precancerous lesions by exposing the affected cells to amino or pyridylamino cyclobutane derivatives.

6 Claims, No Drawings

METHOD FOR TREATING NEOPLASIA WITH AMINO OR PYRIDYLAMINO CYCLOBUTENE DERIVATIVES

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical displasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulceration and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which causes gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans. Thus, the severe side effects due to induction of apoptosis in normal cells by conventional chemotherapeutics are avoided by these novel therapeutics (see, Van Stolk, et al., *Gastroenterology*, 112 (4): A673, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that induce apoptosis in neoplastic cells (but not substantially in normal cells), for treating patients with neoplastic lesions without substantially inhibiting PGE-2. This invention also involves methods for inducing such specific apoptosis in neoplastic cells by exposing such cells to a pharmacologically effective amount of those compounds described below to a patient in need of such treatment. Such compositions are effective in modulating apoptosis and modulating the growth of neoplasms, but are not suffering from the side effects of conventional chemotherapeutics and NSAIDs.

DETAILED DESCRIPTION OF THE INVENTION

As discussed above, the methods of the present invention utilize compounds of Formula I below

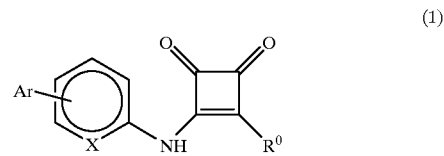

(1)

and pharmaceutically acceptable salts thereof, wherein
Ar is an optionally substituted aryl or heteroaryl ring selected from phenyl, naphthyl, pyridyl, pyrimidyl, pyridazinyl, pyrazinyl, imidazolyl, thienyl, oxazolyl, benzimidazolyl, benzoxazolyl, indolyl or thianaphthenyl, X is CH or N;

$R_0$ is $NR^1R^2$ or hydrogen; and $R^1$ and $R^2$ are independently hydrogen or $C_{1-6}$ alkyl.

Preferred compounds are those wherein Ar is phenyl, or Ar is 2-,3- or 4-pyridyl, 5-pyriridyl, 2- or 4-imidazolyl, 2- or 3-thienyl, 2-oxazolyl, 2-benzimidazolyl, 2-benzoxazolyl, 2-indolyl or 2-thianaphthenyl.

Particularly preferred heteroaryl rings include 3-pyridyl, 2-thiophenyl or 2-indolyl Preferably, Ar is unsubstituted or substituted by at least one group selected from $C_{1-6}$alkyl, $C_{1-6}$alkoxy or hydroxy; and Ar is positioned ortho- or meta- to X.

Also preferred is where X is CH; $R^0$ is $NR^1R^2$; and $R^1$ is hydrogen; and $R^2$ is selected from the group consisting Examples of $C_{1-6}$ alkyl groups include methyl, ethyl, propyl, butyl, pentyl and hexyl, preferably methyl.

Particularly useful compounds in the practice of the methods of this invention include:

3-amino-4-[4-(3-pyridyl)anilino]-3-cyclobutene-1,2-dione, 3-amino-4-[3-(4-imidazolyl)anilino]-3-cyclobutene-1,2-dione, 3-methylamino-4-[3-(5-methyl-4-imidazolyl)anilino]-3-cyclobutene-1,2-dione, 3-dimethylanfino-4-[3-(5-methyl-4-imidazolyl)anilino]-3-cyclobutene-1,2-dione, 3-amino-4-[3-(3-methyl-4-pyridyl)anilino]-3-cyclobutene-1,2-dione, 3-amino-4-[3-(2-oxazolyl)anilino]-3-cyclobutene-1,2-dione, 3-amino-4-[3-(4-pyridyl)anilino]-3-cyclobutene-1,2-dione, 3-amino-4-[3-(3-pyridyl)anilino]-3-cyclobutene-1,2-dione, 3-amino-4-[3-(2-pyridyl)anilino]-3-cyclobutene-1,2-dione, 3-amino-4-[3-(2-thienyl)anilino]-3-cyclobutene-1,2-dione, 3-amino-4-[3-(3-thienyl)anilino]-3-cyclobutene-1,2-dione, 3-amino-4-[3-(2-thianaphthene)anilino]-3-cyclobutene-1,2-dione, 3-amino-4-[3-(5-pyrimidyl)anilino]-3-cyclobutene-1,2-dione, 3-amino-4-[3-(2-benzoxazoyl)anilino]-3-cyclobutene-1,2-dione, 3-amino-4-[3-(2-benzimidazolyl)anilino]-3-cyclobutene-1,2-dione, 3-amino-4-[3-(2-indolyl)anilino]-3-cyclobutene-1,2-dione, 3-amino-4-(3-phenyl)anilino-3-cyclobutene-1,2-dione, 3-amino-4-[3-(2-hydroxyphenyl)anlino]-3-cyclobutene-1,2-dione, 3-amino-4-[3-(2-methoxyphenyl)anilino]-3-cyclobutene-1,2-dione, 3-amino-4-[3-(3-hydroxy-2-pyridyl)anilino]-3-cyclobutene-1,2-dione, 3-amino-4-[3-(2-imidazolyl)anilino]-3-cyclobutene-1,2-dione, 3-amino-4-[6-(4-pyridyl)-2-pyridylanilino]-3-cyclobutene-1,2-dione, and 3-[3-(4-pyridyl)anilino]-3-cyclobutene-1,2-dione, or pharmaceutically acceptable salts thereof.

Compounds of the formula (1) may form pharmaceutically acceptable salts with acids such as hydrochloric, hydrobromic, sulphuric and phosphoric acids.

Compounds of the formula (1) may form pharmaceutically acceptable sets with metal ions, such as alkali metals for example sodium and potassium, or with an ammonium ion.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I, wherein $R_1$, $R_2$, $R_3$ and n are defined as above.

In still another form, the invention is a method of inducing apoptosis in human cells by exposing these cells to an effective amount of compounds of Formula I, wherein $R_1$, $R_2$, $R_3$ and n are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ through $R_3$ etc. are defined as above. The regulation of apoptosis is believed to play an important role in diseases associated with abnormalities of cellular growth patterns such as benign prostate hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostate dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

Each dosage unit for oral administration should contain from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base.

The daily dosage regimen for oral administration should be about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calaculated as the free base. The active ingredient may be administered as required for example from I to 8 times a day or by infusion.

Compounds useful in the present invention can be synthesized by the process reported in WO94/29277, which is incorporated herein by reference. That process comprises reacting a compound of the formula (2):

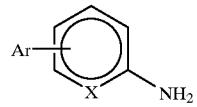

Formula (2)

with a compound of the formula (3):

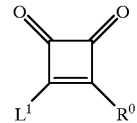

Formula (3)

wherein Ar, X and $R_0$ are as defined above, and $L^1$ is a leaving group, and thereafter optionally forming a pharmaceutically acceptable salt thereof.

Suitably $L^1$ is $C_{1-6}$ alkoxy, halo or $C_{1-6}$ alkylthio, for example methoxy, ethoxy, propoxy or n-butoxy. The reaction reportedly may be performed in the absence of a solvent or in a solvent such as a $C_{1-4}$ alkanol (e.g. methanol or ethanol), acetonitrile or pyridine at ambient or elevated temperature such as 30 to 160° C., conveniently at reflux temperature when in the presence of a solvent.

Compounds of the formula (2) are reportedly known or may be prepared by standard methods. For example, a compound of the formula (2) may be prepared by reacting in the presence of a palladium catalyst a compound of the formula (4) with a compound of the formula (5):

$$Ar^1\text{---}L^2$$

Formula (4)

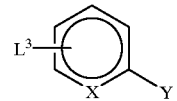

Formula (5)

wherein one of $L^2$ and $L^3$ is $B(OH)_2$ and the other is a suitable leaving group, Y is amino or a precursor thereof, $Ar^1$ is a group Ar as defined above or a precursor thereof, and X is as defined above, and thereafter if necessary
converting a group Y to amino
converting a group $Ar^1$ to Ar.

A suitable leaving group for $L^2$ or $L^3$ is halo, preferably bromo or trifluoromethanesulphonate. Preferably $L^3$ is $B(OH)_2$. Suitably the reaction of a compound of the formula (4) with a compound of the formula (5) is performed in the presence of a base such as triethylamine, barium hydroxide, sodium carbonate or sodium bicarbonate, and when $L^2$ or $L^3$ is trifluoromethanesulphonate in the presence of lithium chloride, in a solvent such as dimethoxyethane, tetrahydrofuran, benzene, ethanol, water or mixtures thereof, at elevated temperature (e.g. 30–150° C.) preferably at the reflux. temperature of the reaction mixture.

An example of a precursor of an amino group is a nitro group which can be reduced to an amino group in conventional manner, e.g. by catalytic hydrogenation. An alternative precursor is a protected amino group such as phthalamido which can be deprotected in conventional manner.

An example of a precursor of the group Ar is when Ar is substituted by an optionally substituted benzyloxy group such as 4-methoxybenzyloxy which can be converted to Ar substituted by hydroxy in conventional manner, e.g. by catalytic hydrogenation.

Compounds of the formula (3) are known or can be prepared by standard methods (e.g., as described in UK patent 1563090).

Compounds of the formulae (4) and (5) are known or may be prepared by standard methods.

Pharmaceutically acceptable acid addition salts of the compounds of the formula (1) may be prepared from the corresponding base of the compounds of the formula (1) in conventional manner. For example the base may be reacted with an acid in a $C_{1-4}$ alkanol, or an ion-exchange resin may be used. The salts of the compounds of the formula (1) may be inter converted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

The synthesis of the compounds of the invention and of the intermediates for use therein are illustrated by the following, non-limiting Examples from the aforesaid PCT applications.

EXAMPLE 1

3-Amino-4-[4-(3-Pyridyl)Anilino]-3-Cyclobutene-1,2-Dione

A solution of 3-(4-aminophenyl)pyridine (0.51 g) and 3-amino-4-ethoxy-3-cyclobutene 1,2-dione (0.42 g) in pyridine (2 ml) is stirred at 80° for 20 hours. The cool mixture is treated with water (15 ml), and the solid filtered off and washed with water and hot methanol. Recrystallation from dimethylformamide gives 0.33 g of the title compound, mp 3224° C. dec.

EXAMPLE 2

3-Amino-4-[-3-(4-Imidazolyl)Anilino]-3-Cyclobutene-1,2-Dione

In a manner similar to that of Example 1, 4-(3-aminophenyl)imidazole (0.48 g) and 3-an 3inoA-ethoxy-3-cyclobutene-1,2-dione (0.42 g) gives 0.40 g of the title compound, mp darkens ca. 300° C. (from dimethylformamide/water).

EXAMPLE 3

3-Methylamino-4-[3-(5-Methyl-4-Imidazolyl)Anilino]-3-Cyclobutene-1,2-Dione

In a manner similar to that of Example 1, 4-(3-aminophenyl)-5-methylimidazole (0.43 g) and 3-ethoxy-4-methylaniino-3-cyclobutene-1,2-dione (0.39 g) gives 0.36 g of the title compound, mp >330° C. (from dimethylformamide).

EXAMPLE 4

3-Dimethylamino-4-[3-(5-Methyl, 4-Imidazolyl)Anilino]-3-Eyclobutene-L,2-Dione

In a manner similar to that of Example 1, 4-(3-aminophenyl)-5-methyl-imidazole (0.57 g) and 3-dimethylamino-4-ethoxy-3-cyclobutene-1,2-dione (0.56 g) gives 0.34 g of the title compound, mp 290–292° C. (from methanol).

EXAMPLE 5

3-Amino-4-[3-(3-Methyl-4-Pyridyl)Anilino]-3-Cyclobutene-1,2-Dione

In a manner similar to that of Example 1, 4-(3-aminophenyl)-2-methylpyridine (0.55 g) and 3-amino-4-ethoxy-3-cyclobutene-1,2-dione (0.42 g) gives 0.28 g of the title compound, mp 205–208° C. (from dimethylformamide).

EXAMPLE 6

3-Amino-4-[3-(2-Oxazolyl)Anilino]-3-Cyclobutene-1,2-Dione

In a manner similar to that of Example 1, 2-(3-aminophenyl)oxazole (0.50 g) and 3-amino -4-ethoxy-3-cyclobutene-1,2-dione (0.44 g) gives 0.56 g of the title compound, mp 312–310° C. (from dimethylformamide),

EXAMPLE 7

3-Amino-4-[3-(4-Pyridyl)Anilino]-3-Cyclobutene-1,2-Dione (a) A stirred mixture of 3-nitrophenylboronic acid (2.00 g), 4-bromopyridine hydrochloride (1.56 g), bis(diphenylphosphino)butanepalladium(II) chloride (0.48 g), sodium bicarbonate (2.69 g), water (30 ml) and 1,2 dimethoxyethane (100 ml) is heated under reflux for 3 hours. The cool mixture is added to water (300 nil) and extracted with chloroform (3×150 ml), and the combined organic extracts washed with water and brine, dried ($MgSO_4$), charcoaled and filtered. The solvent is evaporated to give a residue which is purified by flash chromatography (silica, ether) to give 1.19 g of 4-(3nitrophenyl)pyridine, mp 109–110.5° C. (from acetone/hexane).

(b) A solution of the above nitro compound (1.18 g) in ethanol (30 ml) is shaken with 10% palladium on carbon (0.2 g) under hydrogen (50 psi) for 2.5 hours. Evaporation of the filtered solution gives a solid residue which is recrystallised from ethanol/40–60° Pet. ether to give 0.81 g of 4-(3-aminophenyl)pyridine, mp 167.5–168° C.

(c) In a manner similar to that of Example 1, the above amino compound (0.50 g) and 3-amino-4-n-butoxy-3-cyclobutene-1,2-dione (0.50 g) gives 0.50 g of the title compound, mp 297–300° dec. (from dimethylformamide).

EXAMPLE 8

3-Amino-4-[3-(3-Pyridyl)Anilino]-3-Cyclobutene-1,2-Dione (a) In a manner similar to that of Example 7(a), 3-nitrophenylboronic acid (2.00 g) and 3-bromopyridine (1.26 g) gives 1.22 g of 3-(3-nitrophenyl)pyridine, mp 98.5101° C. (from acetone/hexane).

(b) A stirred mixture of the above nitro compound (1.22 g), stannous chloride dihydrate (6.5 g), conc. hydrochloric acid (6.5 ml) and ethanol (12.5 ml) is heated under reflux for 3.5 hours. Most of the ethanol is evaporated under reduced pressure, and the residue is made alkaline with 40% sodium hydroxide solution. The mixture is extracted with toluene (3×20 ml) and the combined organic extracts washed with water, dried ($MgSO_4$) and evaporated to give a residue which is recrystallised from chloroform/40–60° Pet. ether to give 0.92 g of 3-(3-aminophenyl)pyridine, mp 75–76° C.

(c) In a manner similar to that of Example 1, the above amino compound (0.51 g) and 3-amino-4-ethoxy-3- cyclobutene-1,2-dione (0.42 g) gives 0.45 g of the title compound, mp 256–257° C. (from methanol).

EXAMPLE 9

3-Amino-4-[3-(2-Pyridyl)Anilino]-3-Cyclobutene-1,2-Dione (a) In a manner similar to that of Example 7(a), 3-nitrophenylboronic acid (1.45 g), 2-bromopyridine (1.26 g) and tetmkis(triphenylphosphine)palladium(0) (0.50 g) gives 0.92 g of 2-(3-nitrophenyl)pyridine, mp 71.5–73° C. (from ethanol).

(b) In a manner similar to that of Example 7(b), the above nitro compound (0.92 g) gives 2-(3-aminophenyl)pyridine (0.50 g) as a colourless oil.

(c) In a manner similar to that of Example 1, the above amino compound (0.50 g) and 3-amino-4-n-butoxy-3-cyclobutene-1,2-dione (0.50 g) gives 0.50 g of the title compound, mp 300–303° C. dec. (from dimethylformamide/water).

EXAMPLE 10

3-Amino-4-[3-(2-Thienyl)Anilino]-3-Cyclobutene-1,2-Dione (a) In a manner similar to that of Example 7(a), 3-nitrophenylboronic acid (2.00 g) and 2-bromothiophene (1.30 g) gives 0.69 g of 2-(3-nitrophenyl)thiophene, mp 70–72° C. (from ether).

(b) In a manner similar to that of Example 8(b), the above nitro compound (0.69 g) and stannous chloride dihydrate (3.6 g) gives 0.43 g of 2-(3-aminophenyl) thiophene, mp 30.5–32° C.

(c) In a manner similar to that of Example 1, the above amino compound (0.42 g) and 3-amino-4-ethoxy-3-cyclobutene-1,2-dione (0.34 g) gives 0.35 g of the title compound, mp 297–299° C. dec. (from dimethylfonmamide/water).

EXAMPLE 11

3-Amino-4-[3-(3-Thienyl)Anilino]-3-Cyclobutene-1,2-Dione (a) In a manner similar to that of Example 7(a), 3-nitrophenylboronic acid (1.45 g), 3-bromothiophene (1.30 g) and tetrekis(triphenylphosphine)palladium(0) (0.50 g) gives 1.46 g of 3-(3-nitrophenyl)thiophene, mp 70.5–72.5° C. (from ether/hexane).

(b) In a manner similar to that of Example 8(b), the above nitro compound (0.72 g) and stannous chloride dihydrate (3.75 g) gives 0.38 g of 3-(3aminophenyl)thiophene, mp 86–88° C.

(c) In a manner similar to that of Example 1, the above amino compound (0.37 g) and 3-amino-4-n-butoxy-3-cyclobutene-1,2-dione (0.36 g) gives 0.37 g of the title compound, mp 304–307° C. dec. (from dimethylformamide/water).

EXAMPLE 12

3-Amino-4-[3-(2-Thianaphthenyl)Anilino]-3-Cyclobutene-1,2-Dione (a) In a manner similar to that of Example 7(a), 3-nitrophenylboronic acid (2.20 g), 2-bromothianaphthene (2.81 g) and te~s(triphenylphosphine)palladium(O) (0.25 g) gives 1.19 g of 2-(3-nitrophenyl)thianaphthene, mp 158–159° C. (from acetone).

(b) In a manner similar to that of Example 8(b), the above nitro compound (1.18 g) and stannous chloride dihydrate (5.0 g) gives 0.45 g of 2-(3aminophenyl)thianaphthene, mp 146–147° C.

(c) In a manner similar to that of Example 1, the above amino compound (0.44 g) and 3-amino-4-ethoxy-3-cyclobutene-1,2-dione (0.33 g) gives 0.37 g of the title compound, mp 318–321° C. (from dimethylformamide/water).

EXAMPLE 13

3-Amino-4-[3-(5-Pyrimidyl)Anilino]-3-Cyclobutene-1,2-Dione (a) In a manner similar to that of Example 7(a), 3-nitrophenylboronic acid (2.00 g) and 5-bromopyrimidine (1.27 g) gives 1.16 g of 5-(3-nitrophenyl)pyrimidine, mp 159–160° C. (from acetone).

(b) In a manner similar to that of Example 7(b), the above nitro compound (0.91 g) gives 0.65 g of 5-(3-aminophenyl)pyrimidine, mp 165–167.5° C. (from acetone/hexane).

(c) In a manner similar to that of Example 1, the above amino compound (0.51 g) and 3-amino-4-ethoxy-3-cyclobutene-1,2-dione (0.42 g) gives 0.5 1 g of the title compound, mp 288–290° dec. (from dimethylformamide/water).

EXAMPLE 14

3-Amino-4-[3-(2-Benzoxazoyl)Anilino]-3-Cyclobutene-1,2-Dione

In a manner similar to that of Example 1, 2-(3-aminophenyl)benzoxazole (0.49 g) and 3-amino-4-ethoxy-3-cyclobutene-1,2-dione (0.33 g) gives 0.25 g of the title compound, mp 330–332° C. dec. (from dimethylformamide/water).

EXAMPLE 15

3-Amino-4-[3-(2-Benzimidazolyl)Anilino]-3-Cyclobutene-1,2-Dione

In a manner similar to that of Example 1, 2-(3-aminophenyl)benzlimidiazole (0.52 g) and 3-amino-4-ethoxy-3-cyclobutene-1,2-dione (0.36 g) gives 0.35 g of the tide compound, mp >320° C. (from dimethylformamide/water).

EXAMPLE 16

3-Amino-4-[3-(2-Indolyl)Anilino]-3-Cyclobutene-1,2-Dione

In a manner similar to that of Example 1, 2-(3-aminophenyl)indole (0.48 g) and 3-amino-4-ethoxy-3-cyclobutene-1,2-dione (0.33 g) gives 0.22 g of the title compound, mp ca. 335° C. dec. (from dimethylformamide/water).

EXAMPLE 17

3-Amino-4-(3-Phenyl)Anilino-3-Cyclobutene-1,2-Dione (a) In a manner similar to that of Example 7(b), 3-nitrobiphenyl (2.48 g) gives 1.77 g of 3-aminobiphenyl, mp 27.5–28.5° C.

(b) In a manner similar to that of Example 1, 3-aminobiphenyl (0.51 g) and 3-amino-4-ethoxy-3-cyclobutene-1,2-dione (0.42 g) gives 0.33 g of the title compound, mp 300–301° C. (from dimethylformamide/water).

EXAMPLE 18

3-Amino-4-[3-(2-Hydroxyphenyl)Anilino]-3-Cyclobutene-1,2-Dione (a) A stirred mixture of 2-bromophenol (5.19 g), 4-methoxybenzyl chloride (4.70 g), potassium carbonate (4.15 g) and acetone (30 ml) is heated under reflux for 8 hours. The cool mixture is evaporated under reduced pressure, and the residue is mixed with water (60 ml) and ether (60 ml) and shaken. The aqueous layer is extracted with ether (2×60 ml), and the combined extracts washed with 2M sodium hydroxide solution (20 ml) and water (20 ml), dried (MgSO$_4$) and evaporated to give a solid residue which is recrystallized from ethanol to give 6.18 g of 1-bromo-2-(4-methoxybenzyloxy)benzene, mp 87–90° C.

(b) In a manner similar to that of Example 7(a), 3-nitrophenylboronic acid (1.09 g), 1-bromo-2-(4-methoxybenzyloxy)benzene (1.76 g) and tetrakis(triphenylphosphine)palladium(0) (0.20 g) gives 1.34 g of 2-(4-methoxybenzyloxy)-3'-nitrobiphenyl, mp 99.5–100.5° C. (from acetone/ether).

(c) In a manner similar to that of Example 7(b), the above nitro compound.

(0.86 g) gives 0.29 g of 2-hydroxy-3'-aminobiphenyl, mp 158–161° C. It is reportedly possible to terminate this reaction after adsorption of 3 moles of hydrogen to give 2-(4-methoxybenzyioxy)-3'-aminobiphenyl, mp 68–70° C. (from ether/hexane).

(d) In a manner similar to that of Example 1, 2-hydroxy-3'-aminobiphenyl (0.28 g) and 3-amino-4-n-butoxy-3-cyclobutene-1,2-dione (0.26 g) gives 0.19 g of the title compound, mp 294~297° C. dec. (from dimethylformamide/water).

EXAMPLE 19

3-Amino-4-[3-(2-Methoxyphenyl)Anilino]-3-Cyclobutene-1,2-Dione (a) In a manner similar to that of Example 7(a), 3-nitrophenylboronic acid, (1.45 g), 2-bromoanisole (1.50 g) and tetrakis(triphenylphosphine)palladiuni(0) (0.25 g) gives 0.39 g of 2-methoxy-3'-nitrobiphenyl, mp 67–8T.

(b) In a manner similar to that of Example 7(b), the above nitro compound (0.39 g) gives 174 mg of 2methoxy-3'-aminobiphenyl as an oil.

(c) In a manner similar to that of Example 1, the above amino compound (174 mg) and 3amino-4-n-butoxy-3-cyclobutene-1,2-dione (148 mg) gives 146 mg of the title compound, mp 294–296° C. (from dimethylformamide/water).

EXAMPLE 20

3-Amino-4-[3-(3-Hydroxy-2-Pyridyl)Anilino]-3-Cyclobutene-1,2-Dione (a) A stirred mixture of 2,6-dibromopyridine (3.55 g), benzyl. alcohol (1.63 g), potassium hydroxide (1.68 g), 18-Crown-6 (0.20 g) and toluene (25 ml) is heated under reflux for 30 minutes. The cool solution washed with water and brine, dried (MgSO$_4$) and evaporated to give an oil which is vacuum-distilled (Kugelrohr) to give 3.85 g of 2-benzyloxy-6-bromopyridine, bp 220–225° C./1.0 mm.

(b) In a manner similar to that of Example 7(a), 3-nitrophenylboronic acid (1.09 g), 2-benzyloxy-6-bromopyridine (1.58 g) and tetrakis(triphenylphosphine)palladium(0) (0.40 g) gives 0.95 g of 2-benzyloxy-6-(3-nitrophenyl)pyridine, mp 82.5–83.5° C. (from ether).

(c) In a manner similar to that of Example 7(b), the above nitro compound (0.94 g) gives 0.37 g of 2-(3-aminophenyl)-6-hydroxypyridine, mp 237–239T (from methanol).

(d) In a manner similar to that of Example 1, the above amino compound (0.36 g) and 3-amino-4-n-butoxy-3-cyclobutene-1,2-dione (0.32 g) gives 0.46 g of the title compound, mp 320–322° C. dec. (from dimethylformamide).

EXAMPLE 21

3-Amino-4-[3-(2-Imidazolyl)Anilino]-3-Cyclobutene-1,2-Dione (a) A stirred solution of methyl 3-nitrobenzimidate (7.57 g) and aminoacetaldehyde dimethylacetal (5.57 g) in methanol (20 ml) is heated under reflux for 24 hours. The cool solution is evaporated, and the residue treated with water (9.5 ml) and conc. hydrochloric acid (21 nil). The mixture is heated (steam bath) for 15 minutes and evaporated under reduced pressure. Water (50 ml) is added to the residue and the insoluble solid filtered and washed with water. The filtrate is neutralized with potassium carbonate solution and the precipitated solid filtered and washed with water. The combined solids are charcoaled and recrystallised from ethanol to give 3.87 g of 2-(3nitrophenyl)imidazole, mp 193–194.5° C.

(b) In a manner similar to that of Example 8(b), the above nitro compound (0.72 g) and stannous chloride dihydrate (4.25 g) gives 0.39 g of 2-(3-aminophenyl)imidazole, mp 134–135.5° C.

(c) In a manner similar to that of Example 1, the above amino compound (0.38 g) and 3-amino-4-n-butoxy-3-cyclobutene-1,2-dione (0.40 g) gives 0.34 g of the title compound, mp >340° C. dec. (from dimethylformamide).

EXAMPLE 22

3-Amino-4-[6-(4-Pyridyl)-2-Pyridylamino]-3-Cyclobutene-1,2-Dione

A stirred solution of 2-amino-6-(4-pyridyl)pyridine (0.34 g) and 3-amino-4-n-butoxy-3-cyclobutene-1,2-dione (0.34 g) in pyridine (2 ml) is heated under reflux for 8 hours. The cool mixture is treated with water (15 ml) and the mixture stirred for 1 hour. The solid is filtered, washed with water, ethanol and ether, charcoaled and recrystallised from dimethylformamide to give 73 mg of the title compound, mp >340° C.

EXAMPLE 23

3-[3-(4-Pyridyl)Anilino]-3-Cyclobutene-1,2-Dione

A solution of 4-(3-aminophenyl)pyridine (0.81 g) and 3-n-butoxy-3-cyclobutene-1,2-dione (0.73 g) in ethanol (20 ml) is stirred at ambient temperature for 15 hours. The resultant precipitated solid is washed with methanol and ether and recrystallized from dimethyl formamide to give 0.91 g of the title compound, mp 252–255.5° C.

It will be understood that various changes and modifications can be made in the details of procedure, formulation and use without departing from the spirit of the invention, especially as defined in the following claims.

We claim:

1. A method of treating a mammal having precancerous lesions sensitive to the compounds below comprising administering a pharmacologically effective amount of a compound of Formula I

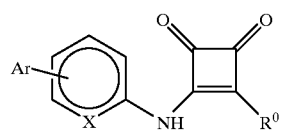

or a pharmaceutically acceptable salt thereof, wherein

Ar is a heteroaryl ring selected from the group consisting of pyridyl, pyrimidyl, pyridazinyl, pyrazinyl, imidazolyl, thienyl, oxazolyl, benzimidazolyl, benzoxazolyl, or indolyl;

X is CH;

$R^0$ is selected from the group consisting of $NR^1R^2$ or hydrogen; and $R^1$ and $R^2$ are independently selected from the group consisting of hydrogen or $C_{1-6}$ alkyl.

2. The method according to claim 1 wherein Ar is 2-,3- or 4-pyridyl, 5p~dyl, 2- or 4-imidazolyl, 2- or 3-thienyl, 2-oxazolyl, 2-benzimidazolyl, 2benzoxazolyl, or 2-indolyl.

3. The method claim 2 wherein Ar is positioned ortho- or meta- to X.

4. The method according to claim 1 wherein the compound is selected from the group consisting of 3-amino-4-[4-(3-pyridyl)anilino]-3-cyclobutene-1,2-dione, 3-amino-4-[3-(4-imidazolyl)anilino]-3-cyclobutene-1,2-dione, 3-methyamino-4-[3-(5-methyl-4-imidazolyl)anilino]-3-cyclobutene-1,2-dione, 3-dimethylamino-4-[3-(5-methyl-4-imidazolyl)anilino]-3-cyclobutene-1,2-dione, 3-amino-4-[3-(3-methyl-4-pyridyl)anilino]-3-cyclobutene-1,2-dione, 3-amino-4-[3-(2-oxazolyl)anilino]-3-cyclobutene-1,2-dione, 3-amino-4-[3-(4-pyridyl)anilino]-3-cyclobutene-1,2-dione, 3-amino-4-[3-(3-pyridyl)anilino]-3-cyclobutene-1,2-dione, 3-amino-4-[3-(2-pyridyl)anilino]-3-cyclobutene-1,2-dione, 3-amino-4-[3-(2-thienyl)anilino]-3-cyclobutene-1,2-dione, 3-amino-4-[3-(3-thienyl)anilino]-3-cyclobutene-1,2-dione, 3-amino-4-[3-(5-pyrimidyl)anilino]-3-cyclobutene-1,2-dione, 3-amino-4-[3-(2-benzoxazoyl)anilino]-3-cyclobutene-1,2-dione, 3-amino-4-[3-(2-benzimidazolyl)anilino]-3-cyclobutene-1,2-dione, 3-amino-4-[3-(2-indolyl)anilino]-3-cyclobutene-1,2-dione, 3-amino-4-[3-(3-hydroxy-2-pyridyl)anilino]-3-cyclobutene-1,2-dione, 3-amino-4-[3-(2-imidazolyl)anilino]-3-cyclobutene-1,2-dione, 3-amino-4-[6-(4-pyridyl)-2-pyridylamino]-3-cyclobutene-1,2-dione, or 3-[3-(4-pyridyl)anilino]-3-cyclobutene-1,2-dione, or a pharmaceutically acceptable salt thereof.

5. A method for inhibiting the growth of neoplastic cells sensitive to the compounds below comprising exposing the cells to a growth inhibiting effective amount of a compound of Formula I or pharmaceutically acceptable salt thereof:

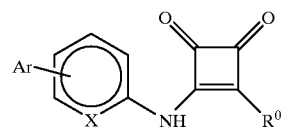

or a pharmaceutically acceptable salt thereof, wherein

Ar is a heteroaryl ring selected from the group consisting of pyridyl, pyrimidyl, pyridazinyl, pyrazinyl, imidazolyl, thienyl, oxazolyl, benzimidazolyl, benzoxazolyl, or indolyl;

X is CH;

$R^0$ is selected from the group consisting of $NR^1R^2$ or hydrogen; and $R^1$ and $R^2$ are independently selected from the group consisting of hydrogen or $C^{1-6}$ alkyl.

6. A method for inhibiting the growth of neoplastic cells sensitive to the compound below comprising exposing the cells to a growth inhibiting effective amount of 3-Amino-4-[3-(4-Imidazolyl)Anilino]-3-Cyclobutene-1,2-Dione or a pharmaceutically acceptable salt thereof.

* * * * *